United States Patent [19]
Coughlin et al.

[11] Patent Number: 5,252,220
[45] Date of Patent: Oct. 12, 1993

[54] PREPARATION OF ANALYTICAL SAMPLES BY LIQUID-LIQUID EXTRACTION USING MICROPOROUS HOLLOW-FIBER MEMBRANES

[75] Inventors: Robert W. Coughlin, Storrs; Edward M. Davis, Cheshire, both of Conn.

[73] Assignee: SymBiotech Incorporated, Wallingford, Conn.

[21] Appl. No.: 411,683

[22] Filed: Sep. 25, 1989

[51] Int. Cl.⁵ .............................................. B01D 61/28
[52] U.S. Cl. .................................... 210/644; 210/649
[58] Field of Search .............. 210/634, 638, 644, 649, 210/321.65; 435/315

[56] References Cited

U.S. PATENT DOCUMENTS

| | | | |
|---|---|---|---|
| 3,956,112 | 5/1976 | Lee et al. | 210/644 |
| 4,516,580 | 5/1985 | Polanyi | 210/321.63 X |
| 4,789,468 | 12/1988 | Sirkar | 210/321.65 X |
| 4,822,491 | 4/1989 | Ostertag | 210/638 |
| 4,865,973 | 9/1989 | Kollerup et al. | 210/644 X |
| 4,906,577 | 3/1990 | Armstrong et al. | 435/315 X |

Primary Examiner—Frank Spear

[57] ABSTRACT

Method and apparatus are provided for accomplishing improved liquid-liquid extraction employing microporous hollow-fiber membranes. A number of possible modes of liquid-liquid extraction are possible according to the invention.

23 Claims, 2 Drawing Sheets

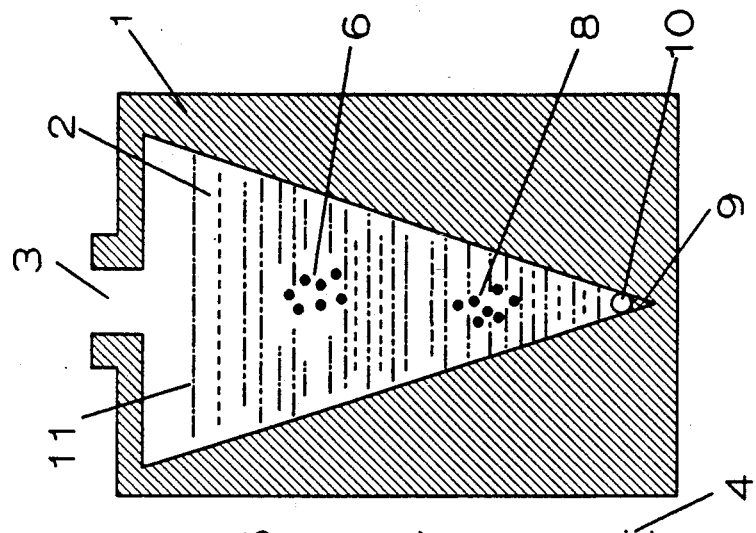
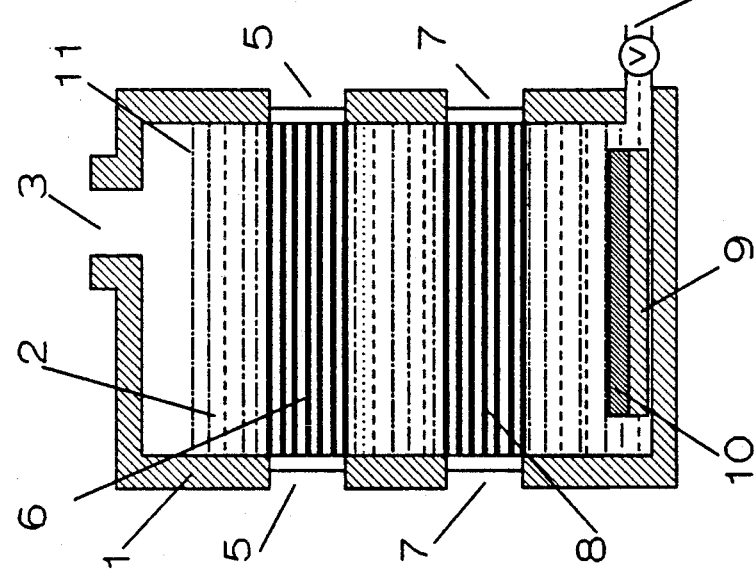

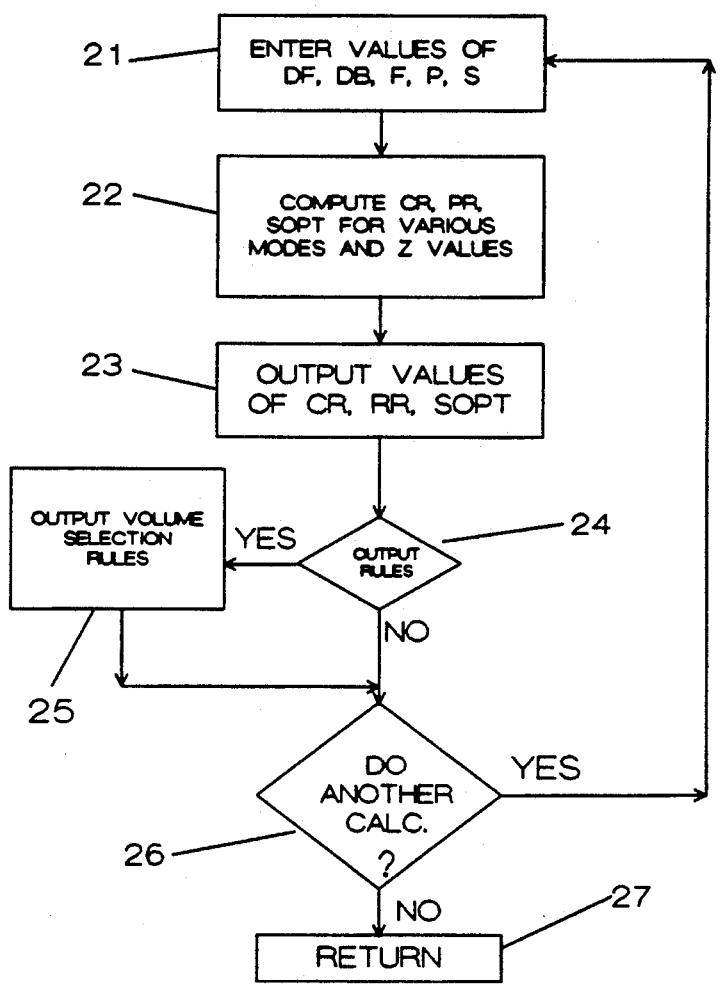

PREPARATION OF ANALYTICAL SAMPLES BY LIQUID-LIQUID EXTRACTION USING MICROPOROUS HOLLOW-FIBER MEMBRANES

BACKGROUND OF THE INVENTION

The present invention provides method and apparatus for concentration of a dissolved component in a liquid sample by means of liquid-liquid extraction using microporous hollow-fiber membranes, e.g. for the purpose of preparation of analytical samples for assay. It has been found that the present invention provides improved and more convenient sample preparation by liquid extraction and permits the optimum selection of several possible modes of operation as well as selection of important operating variables in the method and in the use of the apparatus.

Liquid-liquid extraction (herein sometimes referred to as LLE) is a general and widely used method of preparing samples for later assay by liquid chromatography, gas chromatography, spectrophotometry and other analytical methods. LLE is particularly useful when the compound to be assayed is lipophilic as in the case of a fat soluble drug. In such a case, the solute (i.e. the drug) would be extracted from the analytical sample (e.g., a serum or urine sample) into a liquid solvent (often an organic or hydrocarbon solvent). It could then be back-extracted (or stripped) from the solvent into another liquid, often aqueous and referred to herein as the stripping phase, the product liquid or the product phase. LLE helps to free the solute (e.g., a drug) from interfering substances and can concentrate the solute as well. During forward extraction LLE will tend to concentrate a solute compound in an organic solvent liquid, if the compound is more soluble in the organic solvent liquid than in an aqueous analytical sample. The equilibrium condition of two immiscible phases in contact is often expressed in terms of a distribution coefficient, D, herein defined as:

$$D = \text{(equilibrium concentration of solute in organic solvent phase)/(equilibrium concentration of solute in aqueous phase)} \quad (1)$$

A value of D greater than unity states that the organic phase is favored over the aqueous phase by the solute of interest. A "forward" extraction of a solute from an aqueous feed liquid phase to an organic solvent liquid phase is favored by a distribution coefficient greater than unity as defined by the foregoing equation (1). Back extraction or stripping of a compound from organic solvent liquid to aqueous stripping liquid is favored by a distribution coefficient smaller than unity as defined by the foregoing equation. It is often possible to adjust the distribution coefficient to a favorable value by choosing suitable conditions of pH, temperature and other conditions.

For ease of notation and uniformity, the liquid sample-to-be-analyzed will often be referred to herein as the feed, feed liquid or feed phase, the solvent as solvent liquid or solvent phase (the solvent liquid will often be a hydrocarbon or organic solvent, including organic solvents containing reverse micelles) and the stripping liquid as product, product phase, product liquid or stripping phase. The use of LLE for preparation of analytical samples is further discussed in the following references: D. N. Bailey and M. Kleiner, J. Anal. Toxicology, 8, 26 (1984): E. H. Forester and M. F. Mason, J. Foren. Sci, 19, 155 (1974); I. Sunshine (ed), *Handbook of Analytical Toxicology*, CRC Press, Cleveland (1969).

In addition to being a traditional method of analytical sample preparation, LLE is also a unit operation of chemical engineering used for stage-wise and continuous operations on a larger scale. The smaller-scale use of LLE for analytical sample preparation is generally a batch process, whereas the traditional use of LLE as a larger-scale unit operation is generally a continuous-flow operation. The latter use of LLE is described generally in McCabe, W. L. and Smith, J. C., *Unit Operations of Chemical Engineering*, 3rd Ed., McGraw-Hill, N.Y., 1976, pp. 465–800.

Traditional LLE applied to analytical sample preparation requires the handling of several different liquids, is labor intensive requiring considerable manual manipulation, employs considerable volumes of solvents that are often toxic and suffers from problems such as formation of emulsions which are slow and difficult to separate. For such reasons a new approach has gained favor in recent years in which an organic solvent phase is bonded to a solid support such as silica. This modern innovation is often called solid phase extraction or SPE. SPE is described further by the following references: Tibbins, B.: Nature, 334, pp. 273–274, 21 Jul. 1988; Amer. Biotech. Lab, 5, (1), pp. 25–31 (1987); Amer. Labor News, p. 8, Jun., 1987; Majors, R. E., LC-GC, 4 (10), pp. 972–9844 (1986); McDowell, R. D., et al: J. Pharm. Biomed. Anal., 4 (1), pp. 3–21 (1986).

SUMMARY OF THE INVENTION

The present invention provides improved analytical sample preparation using LLE by employing microporous hollow fibers to manage and control the LLE process. This approach overcomes some of the problems of traditional LLE mentioned supra, and avoids many problems of SPE such as: lack of flexibility in choosing the SPE solvent phase from only those bonded phases available commercially, requirements of large volumes of solvent to condition the SPE solid phase, and solid waste disposal of the spent SPE solid phase after use. The application of microporous hollow fiber membranes (hereinafter sometimes referred to as MPHFM's) to LLE has been earlier disclosed by Cussler, E. L., et al in European Patent Application No. 87304204.8 (European Patent Office Publication No. 0246065; A1). Kiani, A., et al, Journal of Membrane Science, 20, pp. 125–145 (1984) disclose an LLE process employing a planar microporous hydrophobic membrane having an immobilized liquid-liquid interface. However, each of the latter disclosures have been concerned mainly with LLE by continuous flow processes on a large scale. Surprisingly, we have discovered that performing LLE by microporous hollow fibers on a smaller scale batch operation suitable for analytical sample preparation can entail choices regarding novel methods and modes of operation and novel device aspects, as we disclose hereinbelow. We also disclose improved method and apparatus for LLE.

Liquid-liquid extraction processes typically involve a liquid feed containing a solute and an immiscible liquid extractant solvent. Mass transfer of the solute can occur at an interface between the two immiscible phases. It is typical in these processes to attempt to increase their efficiency for mass transfer by maximizing the interfacial surface area between the two phases. Traditionally, LLE processes have been carried out in devices such as packed towers, mixer-settlers, etc., which seek to optimize this interfacial surface area. The intimate mixing that often occurs in these devices often, however, leads to the formation of stable emulsions of the two phases, thereby inhibiting phase separation and product recovery. Traditional LLE systems have avoided using liquids having similar densities, a situation which appears to promote this problem of emulsion formation.

The present invention uses at least one microporous hollow fiber membrane to establish a support for interfacial contact between the two immiscible liquids. When such a microporous membrane is wet with a liquid fluid, the fluid fills the pores of the membrane. If a second liquid immiscible with the liquid in the pores is then allowed to contact the membrane on one side of the membrane, an interfacial contact area is established on that side of the membrane at its surface. This interface is stabilized at the membrane surface by maintaining a higher pressure on the non-wetting liquid than on the wetting liquid, but with said pressure on the non-wetting liquid lower than that necessary for the non-wetting liquid to displace significantly the wetting liquid from the pores of the membrane. (This stabilization requirement has been discussed by Kiani, et al and can also result in the liquid-liquid interface being established within the pores of the membrane.) When the liquid-liquid extraction interface is established at the surface of the microporous membrane, or within its pores, in the LLE process described herein, the problems discussed above for traditional liquid-liquid extraction systems can be avoided.

The solute extracted by the present invention can comprise virtually any species which is soluble in both the feed and the extractant solvent. Both organic and inorganic species can be separated by means of the present invention. Further, polymeric species, especially proteins, having a diameter of less than about the membrane pore size, can be separated by the present process. Still further, multiple solute species can be separated by the present invention. Preferred solutes comprise biological compounds, such as, but not limited to, polypeptides and proteins, and bioaffecting compounds, such as, but not limited to, drugs, pharmaceuticals, enzymes, vitamins, and hormones. Still further, the present invention can be used to extract other inorganic and organic species, including pesticides, chlorinated organic compounds, fuels, petrochemicals, metal ions and metal complexes and mixtures thereof.

Preferred MPHFM materials include polyolefins, cellulose esters polymers, polyamides, polyacrylamides, poly(sulfonated styrene), glass, polysulfones, and polyacrylics. Most preferred are cellulose acetate polymers, polyethylene, polypropylene, polymethylpentene, and polytetrafluoroethylene.

Preferred microporous membrane structures include a microporous membrane having a thickness of 1–75 microns, an average pore size of 50–2000 angstroms, and a porosity of from less than 1% up to about 99%. In the case of microporous hollow fiber membranes, it is preferred that such membranes have a wall thickness of 1–75 microns, an inner diameter of 3–1500 microns, an average pore size of 50–2000 angstroms, and porosity of from less than 1% up to about 99%. Celgard TM microporous membranes, especially Celgard X20 TM microporous hollow fibers (which are commercially available from Celanese Separations Products, Charlotte, N.C.) are typical preferred types.

According to the present invention, sample preparation by LLE is made more convenient by employing microporous hollow fiber membranes in a process and device which permits either sequential or simultaneous contacting of immiscible liquid phases, which provides for convenient mixing to increase mass transfer rates, which provides evaporation of the solvent liquid (after forward extraction of a solute from a feed liquid into the solvent) in order to enhance recoveries, and which also provides a computational system for deciding on a mode of operation, e.g. whether to operate sequentially or simultaneously, for deciding further whether to use an evaporation step if operating sequentially and also in deciding upon the relative volumes of solvent and stripping solution to use in the various cases.

An object of the present invention is to provide a process for analytical sample preparation by LLE using microporous hollow fibers that is convenient and has enhanced rates of mass transfer.

It is a further object that said process be operable in a sequential or simultaneous mode regarding the contacting of the liquid phases (feed phase, solvent phase and stripping or product phase).

It is yet another object to provide for evaporation of solvent between sequential forward and back extraction when the process operates in the sequential mode.

It is still another object to provide for total evaporation of solvent after a forward extraction step of solute from feed liquid to solvent liquid.

Yet another object is to provide for single-step LLE from a feed liquid to a solvent liquid.

Still another object is to provide LLE with the use of a solvent supported in the pores of MPHFM's.

It is yet another object to provide an apparatus for convenient LLE of samples using microporous hollow fibers that provides enhanced mass transfer rates and, if desired, can accomplish evaporation of the solvent liquid after a forward LLE step.

Another object is to provide apparatus which can be used to accomplish LLE conducted according to several different modes of operation.

Yet another object is to provide a computational system to aid in deciding on mode of operation, e.g., whether to use the process and apparatus provided by the present invention in the single-step, supported-solvent, sequential or simultaneous modes, whether and to what extent to evaporate solvent liquid after a forward extraction step, and for deciding how to choose the relative volumes of solvent liquid, stripping or product liquid and feed liquid for a particular selected mode of operation.

The foregoing and additional objects will become apparent to one skilled in the art who examines the description of the invention disclosed herein.

BRIEF DESCRIPTION OF THE DRAWINGS

FIG. 1 depicts schematically a side-view cross-sectional diagram and an end-view cross-sectional diagram of an apparatus for liquid-liquid extraction with MPHFM's according to the present invention.

FIG. 2 depicts a flow diagram of a computer-program system for computing and outputting product-recovery ratios and product-concentration ratios of the various modes in which the apparatus and processes of the present invention can be operated, as well as for outputting rules for selecting optimum liquid volumes for use in the various possible modes of the present invention.

DETAILED DESCRIPTION OF THE INVENTION

The present invention provides process and apparatus for LLE using microporous hollow-fiber membranes (herein sometimes referred to as MPHFM's) in which mass transfer rate is enhanced, in which forward and back extraction can be conducted either sequentially or simultaneously, in which evaporation of solvent can be employed to concentrate the solvent liquid after a forward extraction step. The invention also provides a computational system which indicates how and in which mode to operate (i.e., simultaneously, simultaneously with membrane-supported solvent, sequentially with evaporation, sequentially without evaporation, single step) and further indicates the preferred volumes of feed liquid, solvent liquid and stripping liquid that should be used relative to each other, as well as the effect of evaporating different amounts of solvent.

The way in which the liquid-liquid extraction interface is presumed to be established within a microporous membrane is shown pictorially by Cussler, et al, and Kiani, et al, each cited earlier.

The present invention is directed toward enhancing mass transfer rates during extraction of a solute between a liquid on one side of a microporous membrane and another immiscible liquid, with a liquid-liquid, mass-transfer interface established at or inside the said membrane, the mass transfer rate enhancement being caused by agitation or mixing of at least one of the immiscible liquids. A preferred embodiment includes mixing the liquid phase which is situated on the outside of the lumens of microporous hollow fiber membranes (MPHFM's). The said outer liquid can be mixed, for example, by imposing mechanical vibrational waves on said liquid, or by causing gas bubbles to pass through said liquid.

Using MPHFM's it is possible to conduct forward extraction and back extraction simultaneously by flowing feed liquid and stripping liquid simultaneously through the lumens of separate MPHFM's immersed in the solvent liquid with which neither the feed liquid nor stripping liquid is miscible. It is possible that feed liquid and stripping liquid be miscible with each other so long as each of them is immiscible with the solvent. By this arrangement, solute can be extracted from the feed liquid into the solvent liquid in forward extraction and thence into the stripping liquid by back extraction all at the same time. Similar simultaneous operation can also be accomplished by filling the pores of a MPHFM with solvent and then contacting the solvent filled MPHFM with feed liquid on one side of the membrane and stripping liquid on the other side. This latter type of simultaneous operation is also referred to herein as the use of a supported solvent or supported solvent membrane.

LLE is practiced more traditionally in a sequential mode by first contacting feed liquid and feed-immiscible solvent, then separating feed and solvent, then contacting the solvent with a solvent-immiscible stripping liquid (product liquid). Sequential LLE can be accomplished, for example, by immersing one or more MPHFM's into a solvent which enters its pores, then flowing an immiscible feed liquid through the lumens of the MPHFM's, thereby causing solute to be forward extracted from the feed liquid into the solvent liquid. Stripping liquid is then next flowed through the lumens of MPHFM's immersed in the solvent (either those fibers through which feed liquid passed first, or other fibers immersed in the solvent) thereby causing solute to be back extracted from solvent to immiscible stripping liquid. It will often be possible to greatly enhance the overall operation of forward extraction followed by sequential back extraction by further concentrating the solute in the solvent between the steps of forward and back extraction. A preferred means of causing said further concentration is to evaporate the solvent partially, leaving unevaporated solute behind in the residual solvent liquid.

In many cases a single-step forward LLE of solute from feed to solvent liquid may be sufficient sample preparation. Such may often be the case in preparing samples for assay by gas chromatography of the resulting solution of solute in solvent liquid. This solution can also be concentrated by evaporation, if desired, before injecting it into a gas chromatograph. The method and apparatus of the present invention using MPHFM's are also especially suitable for sample preparation by single-step LLE.

Although mass transfer rate enhancement is always desirable, there are many other choices involved in the application of MPHFM's to sample preparation by LLE. One must choose whether to operate sequentially or simultaneously and if sequentially, whether to employ evaporation to concentrate the solvent. Furthermore, for a given volume of feed liquid, one must also chose the volume of solvent liquid and stripping liquid to employ to obtain favorable results. The present invention also provides a computational system to indicate preferred modes of operation and preferred liquid volumes to employ.

FIG. 1 shows in sideways and in end-on cross sectional views an embodiment of the present invention in the form of a device for LLE which utilizes MPHFM's. The body of the device 1 contains solvent liquid 2 which can be added via port 3 and removed via port 4. Other ports not shown can also be provided for adding and removing solvent. Fittings 5 provide connections to the lumens of an upper bundle 6 of hollow fibers. Additional fittings 7 provide connections to another lower bundle 8 of microporous hollow fibers. The fibers are cemented or potted into the fittings 5 and 7 by a suitable adhesive (e.g. epoxy) in a way well known in the art. The hollow fiber bundles 6 and 8 can be intimately intertwined if desired, but this is not shown in FIG. 1. Such intertwining would be desirable for simultaneous mode operation but not for sequential mode with evaporation. Fittings 5 and 7 can be connected to external supplies of sample feed liquid or stripping liquid using tubing and pumps (not shown) or hypodermic syringes (not shown) which connect to said fittings. An electric heating element 9 is shown disposed along the bottom of the chamber containing the solvent liquid 2 in order to aid solvent evaporation if desired; the connecting wires to supply electric power to heating element 9 are not shown in FIG. 1. A sparger 10 which is supplied with gas via a port (not shown) is also disposed along the bottom of the solvent chamber where it can supply gas bubbles which will rise through the solvent liquid 2, and thereby help to mix the solvent. The sparger 10 can be a microporous hollow fiber, a porous glass frit or some other means of introducing bubbles that is known in the art. These bubbles can also assist in evaporating the solvent liquid in addition to mixing it. The heating means 9 need not always be immersed in the solvent as shown in FIG. 1; another embodiment could employ instead a heating element in the path of the sparging gas in order to heat the gas which would in turn supply the required enthalpy of evaporation to the evaporating solvent. The heating means could also be embedded in the wall of the apparatus of FIG. 1, or the apparatus may be placed on a heating unit. Other means not shown can also be employed to cause mixing of the solvent, e.g., a Vortex mixer or other mechanical or piezoelectric vibrator can be attached to the device to produce mixing. If evaporation of solvent liquid 2 is desired, the heating element 9 or bubbles from sparger 10, or both, can be used to cause evaporation of solvent, in which case the solvent liquid level 11 will fall and solvent vapors can exit from the device via port 3. A very important feature of the device of FIG. 1 is the tapered nature of the solvent chamber which is smaller in horizontal cross section near the bottom than near the top. This permits a large reduction in solvent volume during evaporation, without a proportional decrease in solvent depth. For example, the triangular cross section of the solvent chamber shown in FIG. 1 permits a 75% decrease in volume of solvent by evaporation while the solvent depth decreases by only 50%. Other cross-sectional shapes, e.g. a cusp, can magnify even further the ratio of volume evaporated to decrease in depth.

The device of FIG. 1 is operated in the simultaneous mode (i.e., forward and back extraction occurring simultaneously) by supplying sample feed liquid and stripping liquid simultaneously into the lumens of the two fiber bundles 6 and 8 so that one bundle is filled with feed liquid and the other with stripping liquid; solvent liquid 2 is also simultaneously added via port 3 to submerge the fiber bundles 6 and 8 as shown in FIG. 1. If the fibers are hydrophobic then it may often be preferable to add aqueous feed and stripping liquid to the lumens after adding an organic solvent liquid through port 3. If the fibers are hydrophilic, then it may often be preferable to add the liquids in the opposite sequence. Cussler et al and Kiani et al, each cited supra, provide useful teachings on how to wet and fill the pores of MPHFM's with liquid, including the effects of the sequencing of contacting with different liquids. Feed and stripping liquids can flow through the apparatus, or one or both may remain stationary in the lumens during the simultaneous extraction and stripping process especially if it is desired to use only small volumes of feed and stripping liquids. If both feed and stripping liquids flow simultaneously, the relative sense of their flow directions may be either co-current or countercurrent. The extraction path of the solute will be from the feed liquid, into the solvent liquid (forward extraction), and then from solvent liquid 2 into the stripping liquid (back extraction). Mixing of the solvent 2, e.g. by bubbling gas through sparger 10 will tend to speed up the rate of the combined, simultaneous extraction and stripping process.

A special case of simultaneous-mode operation of the device of FIG. 1 is operation with a solvent liquid supported in the pores of the fibers. To accomplish this type of operation, the solvent can first be contacted with the MPHFM's that are wet by the solvent, thereby causing the membrane pores to fill with solvent, then excess solvent is removed from the fiber lumens, feed liquid is flowed into the fiber lumens and stripping liquid is flowed into the outer tapered chamber of the device of FIG. 1. The locations of feed liquid and stripping liquid can also be reversed. Gas bubbles are sparged from sparger 10 to mix the liquid in the outer chamber. The extraction pathway for the solute is then from feed liquid on one side of the MPHFM walls, into the solvent supported in the pores of the MPHFM's and then into the stripping liquid on the other side of the MPHFM walls. It may often be advantageous to operate in this supported liquid membrane mode using only the lower MPHFM bundle 8 so that smaller volumes of feed liquid and stripping liquid can be employed conveniently. Supported liquid membrane operation is often advantageous if the solvent can be conveniently maintained in the membrane pores during the duration of the extraction operation.

For operation in the sequential mode, feed liquid can be fed first to the lumens of the MPHFM bundles 6 and 8, then solvent can be added through port 3 thereby submerging all the fibers under solvent liquid. Similar teachings apply to the sequence of filling lumens and adding solvent as in the case of simultaneous-mode operation supra. After extraction of solute from feed liquid to solvent liquid, the feed liquid can be removed from the fiber lumens and replaced therein by stripping liquid whereupon solute passes from solvent liquid 2 in the outer chamber to stripping liquid in the lumens of the fibers 6 and 8. The solvent 2 is mixed during the extraction and during the back extraction or stripping processes by sparging gas bubbles through sparger 10, or by other means.

For operation in the sequential mode with intervening evaporation, the solvent 2 is partially evaporated after the forward extraction step but before the back-extraction or stripping step. Evaporation can be accomplished by heating using heating element 9 and it can be further enhanced by bubbling gas through sparger 10. A heating element can also be disposed in the gas-feed stream to heat the sparging gas before it enters the solvent liquid as bubbles. After evaporation has caused the solvent liquid level 12 to fall to a position between fiber bundles 6 and 8, but with lower bundle 8 remaining submerged, then evaporation is discontinued and back extraction is commenced from solvent 2 to the stripping liquid which is now placed in the lumens of the fibers in bundle 8. Before evaporation begins it will usually be preferable to remove the feed liquid from upper fiber bundle 6 but to replace feed liquid with stripping liquid in lower fiber bundle 8.

As in the case of simultaneous-mode operation, it is possible to operate with the feed and stripping liquids in the fiber lumens either flowing or stationary during extraction and back-extraction performed in sequence.

In any mode of operation, after a desired amount of the solute has entered the stripping liquid, the stripping liquid is collected and used for further assay. Whether the liquids in the fiber lumens are caused to flow or held stationary will depend on circumstances; either option is possible independent of whether operation is simultaneous, sequential or by supported liquid membrane. Generally, flowing liquids will increase mass transfer rates but using flow may also tend to increase unfavorably the volumes of liquid employed. Generally, mass transfer rates will be improved by flow of the liquids in the lumens and by mixing, e.g. by sparging gas bubbles through the liquid in the outer chamber exterior to the MPHFM's.

For favorable operation of the sequential mode with evaporation, it is important that the solvent be more volatile than the solute to avoid losing significant amounts of the solute which, if sufficiently volatile, could vaporize and leave the apparatus with the solvent vapors. If heating is used to cause evaporation, then it may be important to employ temperatures which do not cause substantial decomposition of the solute. To avoid decomposition of heat-sensitive compounds gas sparging alone can be used to cause evaporation without heating. In many cases, the lumens of the MPHFM's will not contain liquid during an evaporation step and, if so, gas can be bubbled through such MPHFM's into the solvent thereby furthering the evaporation.

A very important special mode of operation is that which occurs when substantially all of the solvent is evaporated after the forward extraction step. Such total evaporation will leave a concentrated residue of solute in the solvent chamber. A small amount of liquid can then be added to the solvent chamber to dissolve the solute residing there, thereby providing a product liquid containing concentrated solute. This last step is more properly called dissolution rather than back extraction. This mode of operation with total evaporation of the solvent involves a forward extraction of solute from feed liquid in MPHFM lumens into external solvent liquid, followed by substantially complete evaporation of the solvent, followed in turn by addition of another liquid (which might be called a product liquid and could be another, different solvent) to the solute residue in the outer container. This added product liquid dissolves the solute residue in the outer container and thereby becomes the product liquid containing concentrated solute. In this special case of total evaporation, the product liquid need not be immiscible with the solvent employed in the forward-extraction step.

Yet another mode of operation is single-step forward extraction of solute from a feed liquid to a solvent liquid. This can be accomplished in the device of FIG. 1 by placing feed liquid in the lumens of the fibers 6 and 8 and solvent liquid 2 in the outer container as shown, and extracting the solute from feed to solvent liquid. Mass transfer enhancement by bubbling can speed up the extraction. After extraction, the solvent can be partially evaporated as explained supra if it is desired to concentrate the solvent solution further. It is also possible to accomplish single-step forward extraction in the device of FIG. 1 by placing the solvent liquid in the lumens of the fibers and the feed liquid in the outer container.

The process and device for LLE described supra can be operated in at least several modes, including: (a) simultaneous forward and backwards extraction, (b) simultaneous forward and backward extraction using solvent liquid supported in the pores of said hollow fiber membrane, (c) sequential forward and backward extraction, (d) sequential forward and back extraction with partial evaporation of solvent performed between said forward and back extractions, (e) forward extraction of solute from a feed liquid to a solvent liquid, followed by substantially complete evaporation of said solvent liquid leaving a residue of said solute, followed by dissolution of said residual solute in a product liquid, (f) single-step forward extraction of a solute from a feed liquid to a solvent, followed by evaporation of at least a part of said solvent, (g) single-step forward extraction of a solute from a feed liquid to a solvent liquid. In addition to these choices of modes, choices must also be made of the sizes of the volumes of the various liquids to be employed. To provide guidance in making choices among the several possible modes of operation, calculations of concentration, $C_p$, of solute in product liquid and of the extent of recovery of solute in product liquid can be made by assuming that equilibrium is attained in the apparatus with an assumed process mode. If one is interested mainly in assaying the solute in the stripping liquid, then one usually would want to maximize the concentration of solute in the striping liquid to obtain maximum analytical sensitivity; we term this "analytical use" herein. If one is interested in obtaining greatest recovery of the solute, then one may wish to forego obtaining maximum concentration of solute in the stripping liquid, and use larger volumes of stripping liquid to increase solute recovery; we call this type of application "recovery use" herein.

The following mathematical symbols are defined below to develop methods of computing the equilibrium concentration of solute in the product liquid and the equilibrium recovery of solute in the product liquid for the various modes of operation:

$D_f$ = distribution coefficient for forward extraction; this is also written as DF in computer code notation.

$D_b$ = distribution coefficient for back extraction; this is also written as DB in computer code notation.

$Z$ = fraction of the solvent that is evaporated.

$C_{f1}$ = initial concentration of solute in feed liquid.

$C_{f2}$ = final concentration of solute in feed liquid (after equilibrium is attained).

$C_{s1}$ = initial concentration of solute in solvent liquid ($C_{s1}$ is here assumed to be zero).

$C_{s2}$ = final concentration of solute in solvent liquid (after equilibrium is attained).

$C_{p1}$ = initial concentration of solute in product liquid ($C_{p1}$ is here assumed to be zero).

$C_{p2}$ = final concentration of solute in product liquid (after attainment of equilibrium).

F, S, P = respective volumes of feed liquid, solvent liquid and stripping liquid.

CR = concentration ratio, ratio of solute concentration in the product liquid to that in the feed liquid.

RR = recovery ratio, ratio of the amount of solute in the product liquid to that in the feed liquid.

For Simultaneous Operation

A mass balance which equates the amount of solute initially in the feed liquid ($FC_{f1}$) with the amounts in all three phases in simultaneous equilibrium with each other is:

$$FC_{f1} = FC_{f2} + SC_{s2} + PC_{p2} \qquad (2)$$

The distribution coefficients:

$$D_f = C_{s2}/C_{f2} \qquad (3)$$

and $$D_b = C_{s2}/C_{p2} \qquad (4)$$

are then used to eliminate $C_{f2}$ and $C_{s2}$ from equation (2) with the following result for product-to-feed concentration ratio, CR:

$$CR = C_{p2}/C_{f1} = 1/(D_b/D_f + (SD_b)/F + P/F) \qquad (5)$$

The foregoing equation gives the ratio of equilibrium solute concentration in the product stripping liquid to that initially in the feed liquid. This ratio would usually be maximized for "analytical use". The corresponding solute-recovery ratio, RR, for simultaneous-mode operation, which would ordinarily be maximized for "recovery use", is:

$$RR = (PC_{p2})/(FC_{f1}) = 1/((FD_b)/(PD_f) + (SD_b)/P + 1) \qquad (6)$$

Inspection of equation (5) indicates that maximum CR is obtained with: $D_b$, S and P as small as possible and $D_f$ and F as large as possible Inspection of equation (6) indicates that maximum RR is obtained with $D_b$ F and S as small as possible and with P and $D_f$ as large as possible.

Supported Liquid Membrane Operation

This is a special case of simultaneous operation to which the same equations (5) and (6) apply. However, the volume of solvent, S, is now smaller and corresponds to the volume of the pores $V_p$ (or VP in computer code notation) in the MPHFM's. This value of $V_p$ can be estimated as the volume of the fiber walls multiplied by their fractional porosity. The value of $V_p$ can then be used in place of S in equation (5) and (6). Examination of equations (5) and (6) shows that lowered values of S, such as are possible with supported liquid membranes, lead to higher values of the concentration ratio, CR, and the recovery ratio, RR. However, supported solvent membranes can be unstable and the solvent sometimes can easily flow or evaporate out of the pores during operation.

For Sequential Operation Without Evaporation

The mass balance for forward extraction is:

$$FC_{f1} = FC_{f2} + SC_{s2} \tag{7}$$

The back-extraction is accomplished with pure stripping liquid, for which $C_{p1}=0$. The solvent composition is $C_{s2}$ after forward but before back-extraction, and $C_{s3}$ after back-extraction. The mass balance for back-extraction is:

$$S[C_{s2} - C_{s3}] = PC_{p2} \tag{8}$$

The foregoing equations (7) and (8) can be algebraically manipulated together with the distribution coefficient expressions:

$$D_f = C_{s2}/C_{f2} \tag{9}$$

and $$D_b = C_{s3}/C_{p2} \tag{10}$$

to eliminate $C_{f2}$, $C_{s3}$ and $C_{s2}$ to give:

$$CR = C_{p2}/C_{f1} = 1/\{P/(D_fS) + P/F + D_b/D_f + (D_bS)/F\} \tag{11}$$

and $$RR = (PC_{p2})/(FC_{f1}) = 1/\{F/(D_fS) + 1 + (D_bF)/(D_fP) + (D_bS)/P\} \tag{12}$$

Equation (11) states that CR or $C_{p2}$ is increased by increasing $D_f$ and F and decreasing P and $D_b$. Equation (12) indicates that RR is increased by increasing $D_f$ and P and decreasing F and $D_b$. There is an optimum value of S, $S_{opt} = [PF/(D_bD_f)]^{\frac{1}{2}}$ which maximizes both CR or RR. This expression for $S_{opt}$ can be obtained by taking the partial derivative with respect to S of the right-hand side of either equation (11) or (12), setting the derivative equal to zero, and solving the resulting equation for $S_{opt}$.

Sequential Contacting With Evaporation

If the solvent liquid, originally of volume S during the forward extraction, is evaporated by a fraction Z after forward extraction, then the solvent volume after evaporation and during the back extraction process is $S(1-Z)$. The mass balance for back extraction is then as follows:

$$SC_{s2} = (1-Z)SC_{s3} + PC_{p2} \tag{13}$$

When this equation is solved as before with the mass balance equation (7) for the forward extraction and the two equations (9) and (10) defining the distribution coefficients, the results for CR and RR are:

$$CR = C_{p2}/C_{f1} = 1/\{P/(D_fS) + P/F + ((1-Z)D_b)/D_f + ((1-Z)D_bS)/F\} \tag{14}$$

and $$RR = (PC_{p2})/(FC_{f1}) = 1/\{F/(D_fS) + 1 + ((1-Z)D_bF)/(D_fP) + ((1-Z)D_bS)/P\} \tag{15}$$

By inspection, maximum CR will be obtained for P as small as possible, F and large as possible, and Z as close to 1.0 as possible. In contrast, maximum RR will be obtained with P as large as possible, F as small as possible and Z as close to 1.0 as possible. Use of the derivative calculus as before indicates that once F, P and Z are fixed, then the optimum value of S to maximize either RR or CR is:

$$S_{opt} = [(PF)/((1-Z)D_bD_f)]^{\frac{1}{2}} \tag{16}$$

Equation (16) is obtained by taking the partial derivative with respect to S of either equation (14) or (15), setting the derivative equal to zero, and solving the resulting equation for $S = S_{opt}$. This expression [equation (16)] for $S_{opt}$ is applicable also to the sequential mode without evaporation by setting $Z=0$. Because the starting volume of solvent may be set by the physical dimensions of the apparatus, the last optimum criterion of equation (16) can be restated, for a given value of S, as:

$$(P \cdot F)_{opt} = S^2(1-Z)D_bD_f \tag{17}$$

Thus for maximum CR, P should be as small as possible and F as large as possible and their product should be given by equation (17). Similarly, for maximum RR, P should be as large as possible and F as small as possible and their product should also be given by equation (17). In case equations (16) or (17) are far from being satisfied by the values of P and F selected and the value of S corresponding to the apparatus, it means that there is a mismatch between feed-liquid volume F, product-liquid volume, P and the solvent volume of the apparatus.

Sequential Operation with Complete Evaporation of the Solvent

Equation (14) for CR and equation (15) for RR also apply to the total-evaporation case with $Z=1$ and P=the volume of product liquid that is used to dissolve the solute residue after total evaporation of the solvent. Equation (16) is also applicable and predicts that in the present case of substantially complete evaporation, maximum CR and maximum RR are obtained by making the original volume of solvent liquid as large as possible.

Single-Step Forward Extraction

Equation (7) for the forward-extraction step can be combined with the definition of $D_f$ in equation (3) to eliminate $C_{f2}$ thereby giving:

$$CR = C_{s2}/C_{f1} = 1/[1/D_f + S/F] \tag{18}$$

$$RR = SC_{s2}/FC_{f1} = 1/[F/(SD_f) + 1] \tag{19}$$

Here CR and RR have somewhat different algebraic forms because the product liquid is the solvent liquid in the case of single-step forward extraction. These equations show that CR is increased by increasing F and decreasing S, whereas RR is increased by increasing S and decreasing F. The value of CR or $C_{s2}$ can be further enhanced by evaporation of the solvent after extraction; for example, 50% evaporation can increase $C_{s2}$ by a factor of 2 and 90% evaporation by a factor of ten.

The various foregoing equations for CR and RR may be used with any consistent units for the volume terms F, S and P. It is noted that CR, RR, $D_f$ and $D_b$ are dimensionless as defined herein.

The foregoing equations for CR and RR are developed from mass balance and equilibrium assumptions. As such, they predict the values of CR and RR that would result if equilibrium between the phases were attained. Although considerable contact time may be required to attain equilibrium, the equilibrium-based equations predict the best values of CR and RR that can be realized under equilibrium conditions for a given operational mode and with a given set of distribution coefficients and liquid volumes. Thus these equations permit equilibrium performance by the individual modes of operation to be compared for a given set of distribution coefficients and liquid volumes. Alternatively, the equations for a given mode of operation can be used to indicate how to choose the individual liquid volumes to maximize CR and RR for that particular mode, and with given distribution coefficients. Examination of the equations for CR and RR shows that, for a given set of distribution coefficients and liquid volumes, CR and RR will always be smaller for non-evaporative, sequential operation [equations (11) and (12)] than for simultaneous operation [equations (5) and (6)], because there is an additional term in the denominator of each expression for sequential operation. Sequential operation with evaporation, however, can deliver larger values of CR and RR if the values of Z are made sufficiently close to unity, i.e., if sufficient evaporation of solvent liquid is performed.

The foregoing equations permit a set of rules to be stated regarding how to adjust volumes to increase values of CR or RR. These rules are: (1) For any mode of operation CR is increased by increasing F and decreasing P (or decreasing S in single-step forward extraction where the solvent solution is the product solution). (2) For any mode of operation, RR is increased by decreasing F and increasing P (or increasing S in single-step forward extraction where the solvent solution is the product solution). (3) For simultaneous operation, decreasing S causes CR and RR to increase. (4) To maximize both CR and RR in sequential operation with given values of P and F, there is an optimum value of S equal to $[(PF)/((1-Z)D_bD_f)]^{\frac{1}{2}}$, where Z=fraction evaporated, Z=0 corresponds to sequential operation with no evaporation, and Z=1 corresponds to complete evaporation of solvent after forward extraction, with the total-evaporation step followed by dissolving solute residue in product liquid of volume P. Note that the mathematically predicted optimum value of the solvent volume, $S_{opt}$, may be physically impractical, e.g., it may be too small to submerge the desired number of fibers in a particular device. With total evaporation [Z=1], equation (16) predicts an infinite value of $S_{opt}$, and this means the initial value of S should be chosen as large as possible, i.e. as large as the size of the apparatus permits.

In order to choose the best operational mode for the LLE process with an apparatus such as shown in FIG. 1, this invention provides a data-processing methodology based on the foregoing equations that can compute and output the values of CR and RR for each operational mode, when a given set of liquid volumes and distribution coefficients are supplied. The data processing methodology can also output rules and advice on how best to select the liquid volumes to maximize CR and RR for each mode. Thus the data processing methodology also provides the user with the ability to choose and change the input values of liquid volumes to explore how changing the amounts of the liquid volumes can affect the values of CR and RR for each mode. FIG. 2 depicts a schematic flow chart of a data processing methodology provided by the present invention. Referring to FIG. 2, step 21 is an operation is which the required parameters (e.g., DF, DB, F, P, S, VP) are supplied to the system. In step 22, the values of RR and CR are computed for each operational mode under consideration, using mass balance equations and definitions of DF and DB as, for example, by using at least one mass balance equation developed supra. Values of optimum solvent volumes for sequential operation are also computed in step 22; various extents of solvent evaporation can be included in the calculations, as desired. Step 23 outputs (i.e., supplies) the values computed in step 22, e.g., by printing or by displaying the values on the screen. Test 24 queries the user whether the volume selection rules should be outputted and, if so desired, these rules are outputted by step 25. Test 29 queries the reader whether additional calculations are to be made and transfers system control according to the answer to the query.

Table 1 is an embodiment of the data processing methodology shown in the schematic flow diagram of FIG. 2. Table 1 shows a computer program written in the BASIC computer language using the parameter symbols defined herein and standard BASIC statements. The application and use of the BASIC computer language can be found described in the textbook, *BASIC: A Programmed Text* by S. Hirsch, John Wiley and Sons, Inc. (1975).

TABLE 1

| BASIC COMPUTER PROGRAM LISTING |
| --- |
| 100 PRINT "enter value of forward extraction distribution coefficient" |
| 105 INPUT DF |
| 110 PRINT "enter value of back-extraction distribution coefficient" |
| 115 INPUT DB |
| 120 PRINT "enter value of feed liquid volume" |
| 125 INPUT F |
| 130 PRINT "enter value of stripping-liquid volume" |
| 135 INPUT P |
| 140 PRINT "enter value of solvent volume" |

TABLE 1-continued
BASIC COMPUTER PROGRAM LISTING

```
145  INPUT S
150  PRINT "enter value of membrane pore volume"
155  INPUT VP
160  CRSIM=1/(DB/DF+S*DB/F+P/F)
165  RRSIM=1/(F*DB/(P*DF)+S*DB/P+1)
170  CRSUP=1/(DB/DF+VP*DB/F+P/F)
175  RRSUP=1/(F*DB/(P*DF)+VP*DB/P+1)
176  CRSS=1/(1/DF+S/F)
177  RRSS=1/(F/(F*DF)+1)
180  CRSEQ=1/(P/(DF*S)+P/F+DB/DF+DB*S/F)
185  RRSEQ=1/(F/(DF*S)+1+DB*F/(DF*P)+DB*S/P)
190  SOPT=SQR(P*F/(DB*DF))
195  Z=1
200  FOR I=1 to 4
205  CR(I)=1/(P/(DF*S)+P/F+(1-Z)*DB/DF+(1-Z)*DB*S/F)
206  RR(I)=1/(F/(DF*S)+1+(1-Z)*DB*F/(DF*P)+(1-Z)*DB*S/P)
207  SOPT(I)=SQR(P*F/((1-Z)*DB*DF))
210  Z=Z-.25
215  NEXT I
220  PRINT "VALUES OF CONCENTRATION RATIO:"
225  PRINT "for simultaneous mode"; CRSIM
230  PRINT "for supported solvent membrane";CRSUP
231  PRINT "for single-step forward extr.";CRSS
235  PRINT "for sequential mode, no evap";CRESEQ
240  PRINT "for sequential with 100% evap";CR(1)
245  PRINT "for sequential with 75% evap";CR(2)
250  PRINT "for sequential with 50% evap";CR(3)
251  PRINT "for sequential with 25% evap";CR(4)
255  PRINT "VALUES OF RECOVERY RATIO:"
260  PRINT "for simultaneous mode"; RRSIM
265  PRINT "for supported solvent membrane";RRSUP
266  PRINT "for single-step forward extr.";RRSS
270  PRINT "for sequential mode, no evap";RRESEQ
275  PRINT "for sequential with 100% evap";RR(1)
276  PRINT "for sequential with 75% evap";RR(2)
280  PRINT "for sequential with 50% evap";RR(3)
285  PRINT "for sequential with 25% evap";RR(4)
286  PRINT "Parameters used are
S=";S;"VP=";VP;"F=";F;"P=";P;"DF=";DF;"DB=";DB
287  PRINT "enter cont to continue calculations"
288  STOP
290  PRINT "OPTIMUM SOLVENT VOLUMES FOR SEQUENTIAL MODES:"
295  PRINT "with 100% evap";SOPT(1)
300  PRINT "with 75% evap";SOPT(2)
305  PRINT "with 50% evap";SOPT(3)
306  PRINT "with 25% evap";SOPT(4)
310  PRINT "with 0% evap";SOPT
311  PRINT "optimum solvent volume = SQRT[P*F/((1-Z)*DF*DB)]"
315  PRINT "Parameters used are S";S;" VP";VP;" F";F;" P";P;"
DF";DF;" DB";DB
316  PRINT "PRINT OUT GENERAL RULES? ENTER 1 FOR YES, 0 FOR NO."
317  INPUT ANS
318  IF ANS=0 THEN 324
319  PRINT "For all modes of operation, the concentration ratio,
CR, is increased by making F as large as possible and P as small
as possible (P refers to solvent in the case of
single-step forward extraction)."
320  PRINT "For all modes of operation, the recovery ratio, RR, is
increased by making F as small as possible and P as large as
possible (P refers to solvent in the case of single-step, forward
extraction)."
321  PRINT "For simultaneous operation, decreasing solvent volume,
S or VP, increases both CR and RR."
322  PRINT "For sequential operation the optimum solvent volume
depends on the values of both F and P and is given by
SQRT[P*F/((1-Z)*DF*DB)]"
324  PRINT "Do another calculation? Enter 1 for yes, 0 for no."
325  INPUT ANS
330  IF ANS=1 THEN 100
340  END
```

In operation, the BASIC object program of Table 1 is input into the random access memory (RAM) of a computer under the control of a BASIC software program already present in the RAM. The BASIC software program is generally loaded into the RAM from an input device such as a floppy-disk drive, a hard-disk drive or magnetic tape. The object program can be similarly input or it can be entered via a keyboard console. The results from the operation of the object computer program can be outputted to a printer, a CRT screen, a liquid crystal screen, magnetic or optical media or to another output device. An important embodiment of the present invention is a device as in FIG. 1 in combination with a digital computer, a source program such as a BASIC software source code, an object program such as a BASIC object code as in Table 1, and suitable input and output means in conjunction with the RAM of said computer. Said RAM can contain the object and source programs or receive same as input from an input device.

EXAMPLES

Example 1

Microporous polypropylene hollow fibers of the following characteristics were used: inner diameter equals 381 micrometers; wall thickness equals 29 micrometers; wall porosity equals 40% voids. Twelve fibers were potted into the tip of a 5.75 inch long glass Pasteur pipette; the fibers were long enough to extend past each end of the pipette. Two ml of solvent (a 19 to 1 (v/v) mixture of chloroform and isopropanol) was placed into the pipette (i.e. in the space formed between the inner wall of the pipette and the outer walls of the fibers therein) thereby submerging several inches of fiber length. A feed solution containing 50.6 mg/L of the drug theophylline (solute) was pumped through the lumens of six of the fibers. A stripping solution of 0.1M NaOH solution was simultaneously pumped co-currently through the lumens of the other six fibers. Flow rate of feed solution and stripping solution were equal. Two different flow rates were used. Experiments were performed with mass transfer enhancement by bubbling air through the solvent liquid as well as with no enhancement. The results were as follows:

TABLE 2

| Flow Rate (ml/min) | Contact Time (minutes) | Solute Conc. in Stripping Solution, (mg/L) | FATE % |
|---|---|---|---|
| without bubbling: | | | |
| 0.11 | 27 | 3.0 | 6 |
| 0.50 | 6 | 1.0 | 2 |
| with bubbling: | | | |
| 0.11 | 27 | 5.3 | 10 |
| 0.50 | 6 | 1.7 | 3 |

In Table 2, FATE is the fractional approach to equilibrium defined as: concentration of solute measured in stripping solution divided by concentration of solute that would have been in the stripping solution if the liquids had come to equilibrium. The favorable effect of mixing the solvent by bubbling shown by this example is a surprising result in view of the Cussler et al reference cited supra. Cussler et al show the very favorable results that arise when the liquid filling the pores of the membrane is that in which the solute is most soluble. Their results indicate that transport through the membrane is the controlling transport resistance, and thus it would not be expected that mixing a liquid external to the membrane would enhance transport rate.

Example 2

A device similar to that of Example 1 but containing 18 MPHFM's of the same type as in Example 1 were employed. Two ml of a toluene solvent containing 3 micrograms of the drug desipramine was added to the Pasteur pipette as in Example 1 and 2 ml of M sulfuric acid solution used as a stripping liquid was pumped through all 18 hollow fibers at a flow rate of 0.14 ml/min over a time period of 14 minutes. About 70% of the desipramine in the solvent was back extracted into the stripping solution in the experiment of this example.

Example 3

Computations were carried out for LLE conducted in a device such as shown in FIG. 1. The lower triangular cross section of the outer chamber where the fibers were located was about 2 mm wide at the top, and 2.5 mm deep from the uppermost fibers to the lower apex. This chamber was 10 cm long and was spanned along its long axis by 15 hollow fibers of the type described in Example 1. The volume of the outer chamber was about 252 microliter of which the fibers occupied 198 microliters, leaving 54 microliters to be occupied by solvent liquid. Unless indicated otherwise, computations were conducted for F=100, P=50 and S=50 (all in microliters) and for various stated values of $D_f$ and $D_b$. The results are in Table 3.

TABLE 3

| For $D_f = 100$, $D_b = 10$: | |
|---|---|
| CR = 0.166 | for simultaneous mode. |
| CR = 1.818 | for single-step forward extraction |
| CR = 0.166 | for sequential mode, Z = 0 |
| CR = 0.307 | for sequential mode, Z = 0.5 |
| CR = 0.531 | for sequential mode, Z = 0.75 |
| CR = 1.964 | for sequential mode, Z = 1.0 |
| CR = 1.15 | for sequential mode, Z = 0.5 and optimum solvent volume of 3.16 microliters. |
| For $D_f = 10$, $D_b = 10$: | |
| CR = 0.145 | for simultaneous mode. |
| CR = 1.563 | for single-step forward extraction |
| CR = 0.143 | for sequential mode, Z = 0 |
| CR = 0.264 | for sequential mode, Z = 0.5 |
| CR = 0.456 | for sequential mode, Z = 0.75 |
| CR = 1.688 | for sequential mode, Z = 1.0 |
| CR = 0.5 | for sequential mode, Z = 0.5 and optimum solvent volume of 10 microliters. |
| For $D_f = 1$, $D_b = 1$: | |
| CR = 0.490 | for simultaneous mode. |
| CR = 0.649 | for single-step forward extraction |
| CR = 0.337 | for sequential mode, Z = 0 |
| CR = 0.455 | for sequential mode, Z = 0.5 |
| CR = 0.552 | for sequential mode, Z = 0.75 |
| CR = 0.701 | for sequential mode, Z = 1.0 |
| CR = 0.5 | for sequential mode, Z = 0.5 and optimum solvent volume of 100 microliters. |

Example 4

The device of Example 3 was also investigated for operation in the supported solvent membrane mode. The volume of the solvent in the pores of the 15 fibers was 6.5 microliters, the feed volume was 100 microliters a before, whereas the stripping solution occupied the outer chamber and thus was of volume P=54 microliters. The results of the computation for supported solvent membrane mode are in Table 4.

TABLE 4

| $D_f$ | $D_b$ | CR for Supported Solvent Membrane Mode |
|---|---|---|
| 100 | 10 | 0.775 |
| 10 | 10 | 0.457 |
| 1 | 1 | 0.623 |

Comparing the results of the two foregoing Examples 3 and 4, it is seen that for a LLE system with $D_f$=100 and $D_b$=10, the highest predicted CR is 1.964 for sequential operation with 100% evaporation, S=54 microliters and P=50 microliters. For 50% evaporation, the optimum solvent volume of 3.16 microliters could be impractical if this volume of solvent did not submerge the desired number of fibers.

It is seen in the results of Examples 3 and 4 that, if both a forward and a back extraction are required, the preferred values of CR for the parameters given are predicted for sequential operation with significant evaporation of the solvent. If such an operating mode proved impractical (e.g. because of undesired evaporation of a very volatile solute) then the next most favorable operating mode involving forward and back extraction, supported solvent, might be chosen. If the supported solvent mode proved impractical, (e.g. because of loss of the solvent from the membrane), then the next most favorable operating mode with forward and back extraction, simultaneous operation with unsupported solvent, might be chosen. If no stripping or back extraction is necessary, then it is seen that single-step forward extraction provides favorably large values of solute concentration in the solvent as indicated by relatively large values of CR.

To those skilled in the art to which this invention relates, many changes in construction and widely different embodiments and applications of the invention will suggest themselves without departing from the spirit and scope of the invention. The disclosures and the description herein are purely illustrative and are not intended to be in any sense limiting.

The claims intended to be covered by Letters Patent are:

1. A method of extracting a solute from a sample liquid through at least one microporous hollow fiber membrane and into a solvent liquid that is immiscible with said sample liquid, each of the liquids being in contact with an opposite side of the membrane, wherein the extraction is conducted as a batch operation for preparing a small laboratory sample, as for assay, comprising the steps:
   (a) placing said sample liquid in contact with one side of said membrane and said solvent liquid on the other side of said membrane, or within the pores of said membrane, so as to form an interface between the two liquids at or within said membrane,
   (b) mixing at least one of the liquids while it is in contact with said membrane,
   (c) extracting said solute from said sample liquid into said solvent liquid,
   (d) conducting an additional step chosen from the group consisting of:
      (i) back extracting said solute from said solvent liquid into a stripping liquid that is immiscible with said solvent liquid, and
      (ii) evaporating at least a portion of said solvent liquid.

2. In a process for liquid-liquid extraction of a solute using at least one microporous hollow-fiber membrane, a method for improving the selection of mode of operation from among more than one possible mode using a computer system, comprising the steps:
   (a) selecting and inputting values of parameters characteristic of a liquid-liquid extraction system and the desired volumes of feed liquid, product liquid, solvent liquid and pore volume of said hollow fiber membrane, said values being transferred from an input device means to a memory means,
   (b) selecting an appropriate mass balance relationship for each mode of operation contemplated, said relationship residing within said memory means,
   (c) computing CR or RR values using said mass-balance relationships selected in step b and said values inputted in step a,
   (d) outputting said values of CR and RR computed in step c for use in selecting a mode of operation.

3. The method of claim 2 wherein said modes of operation comprise:
   (a) simultaneous forward and backwards extraction,
   (b) simultaneous forward and backward extraction using solvent liquid supported in the pores of said hollow fiber membrane,
   (c) sequential forward and backward extraction,
   (d) sequential forward and backward extraction with partial evaporation of solvent performed between said forward and back extractions,
   (e) forward extraction of solute from a feed liquid to a solvent liquid, followed by substantially complete evaporation of said solvent liquid leaving a residue of said solute, followed by dissolution of said residual solute in a product liquid,
   (f) single-step forward extraction of a solute from a feed liquid to a solvent, followed by evaporation of at least a part of said solvent,
   (g) single-step forward extraction of a solute from a feed liquid to a solvent liquid.

4. An improved method of preparing a small volume of sample fluid for assay of a solute therein by extracting said solute from said sample fluid through at least one porous hollow fiber membrane and into a solvent fluid that is immiscible with said sample fluid, comprising the steps:
   (a) placing said sample fluid in contact with one side of the membrane and said solvent fluid on the other side of said membrane, or within pores in said membrane, so as to form an interface between the two fluids at or within said membrane,
   (b) mixing at least one fluid while it is in contact with said membrane,
   (c) extracting said solute from said sample fluid into said solvent fluid, and
   (d) conducting an additional step chosen from the group consisting of:
      (i) removing at least a portion of one of the fluids from said membrane and assaying the removed fluid for said solute,
      (ii) back extracting said solute from said solvent fluid into a stripping fluid that is immiscible with said solvent fluid, and
      (iii) evaporating at least a portion of said solvent fluid.

5. The method of claim 4 wherein mixing step b is accomplished by sparging a gas through a liquid fluid in contact with said membrane.

6. The method of claim 4 wherein step d(i) is employed.

7. The method according to claim 6 wherein the volume of fluid within the lumen of said hollow fiber membrane is in the range of about several microliters to several milliliters.

8. The method of claim 4 wherein step d(ii) is employed and forward extraction of said solute from said sample fluid to said solvent fluid according to step c and back extraction from said solvent fluid to said stripping fluid according to step d(ii) are conducted simultaneously, wherein said sample fluid is in the lumen of at least one hollow fiber membrane, wherein said stripping fluid is in the lumen of at least one other hollow fiber membrane, while each of said hollow fiber membranes is immersed in said solvent fluid, and wherein mixing step b is conducted by mixing said solvent fluid while said forward and back extractions occur simultaneously.

9. The method of claim 8 wherein the volumes of said sample fluid, said solvent fluid and said stripping fluid are selected to maximize either the recovery of said solute or the concentration of said solute in said stripping fluid, in accord with a mass balance equation for simultaneous operation.

10. The method according to claim 8 wherein said mixing step b is caused by gas sparging.

11. The method of claim 4 wherein step d(ii) is employed and forward extraction of said solute from the sample fluid to said solvent fluid according to step c and back extraction from said solvent fluid to said stripping fluid according to step d(ii) are conducted simultaneously, wherein said solvent fluid is in the pores of said membrane thereby supporting said solvent fluid in said membrane, wherein said sample fluid is on one side of said membrane and said product or stripping fluid on the other side of said membrane, and wherein mixing step b is conducted by mixing at least one of said sample fluid and said stripping fluid while said forward and back extractions occur simultaneously.

12. The method of claim 11, wherein the volume of said solvent fluid is chosen to fill the pores of said membrane and the volumes of said sample fluid and said stripping fluid are chosen to maximize either the recovery of said solute or the concentration of said solute in said stripping fluid, in accord with a mass balance equation for operation with supported solvent in said membrane.

13. The method according to claim 11 wherein said mixing step b is caused by gas sparging.

14. The method of claim 4 wherein step d(ii) is employed and forward extraction of said solute from said sample fluid to said solvent fluid according to step c is conducted sequentially before back extraction of said solute from said solvent fluid to said stripping fluid according to step d(ii), wherein said sample fluid is in the lumen of at least one hollow-fiber membrane submerged within said solvent fluid as a result of step a, wherein said sample fluid is removed from contact with said solvent fluid before conducting step d(ii), wherein step d(ii) is conducted by introducing said stripping fluid into the lumen of at least one said hollow fiber membrane submerged within said solvent fluid, whereby said solute is stripped from said solvent fluid to said stripping fluid, and wherein at least one of said solvent or stripping fluids is mixed during the back extraction step d(ii).

15. The method of claim 14 wherein said solvent fluid is a liquid and at least a portion of said solvent fluid is evaporated between forward extraction step b and back extraction step d(ii).

16. The method of claim 15, wherein the volumes of said sample, solvent and stripping fluids are chosen to maximize either the amount of said solute recovered or the concentration of said solute in said stripping fluid, as predicted by a mass balance equation for sequential operation with evaporation of said solvent fluid.

17. The method of claim 14, wherein the volumes of said sample, solvent, and stripping fluids are chosen to maximize either the recovery of said solute or the concentration of said solute in said stripping fluid, in accord with a mass balance equation for sequential operation.

18. The method of claim 4 wherein step d(iii) is employed, said solvent fluid is a liquid and said liquid is separated from said sample fluid before conducting evaporation step d(iii).

19. The method of claim 18 wherein substantially all of said solvent liquid is evaporated during the evaporation step d(iii) and at least a part of said residue, if a solid, is re-dissolved in a liquid.

20. The method of claim 19, wherein the volumes of said sample, solvent and product fluids are chosen to maximize either the amount of said solute recovered or the concentration of said solute in said product fluid, in accord with a mass balance equation for sequential operation with substantially complete evaporation of solvent before re-dissolution of said residue.

21. The method of claim 4, wherein at least one mass balance equation and at least one distribution coefficient are employed to compute, for two or more modes of operation, the amount of said solute recovered and the concentration of said solute in a product fluid using the desired volumes of said fluids, and said computed amounts are then used as criteria for selecting the mode of said extractions from among more than one possible mode, then performing the extraction according to the mode selected.

22. In a process according to claim 4, a method for selection and adjustment of values of distribution coefficients and volumes of sample fluid, solvent fluid and product fluid, using a computer system holding within its memory means rules for said selection and adjustment and corresponding to at least each mode of operation recited in claim 3, said rules being based on maximizing either CR or RR by means of mass balance relationships, and comprising the steps of:

(A) choosing a mode of operation from among at least those recited in claim 3, (B) inputting to said memory means from an input device means the choice made in step a, so as to designate rules for selecting and adjusting said values of sample fluid, solvent fluid, product fluid and distribution coefficients, (C) outputting from said memory means to an output device means the rules designated in step b and corresponding to said mode chosen in step A.

23. The method of claim 22 wherein said rules, when for sequential operation, include a relationship for estimating an optimum amount of solvent fluid from the volumes of product fluid and sample fluid, from the values of distribution coefficients and from the fraction of solvent evaporated if an evaporation step is used.

* * * * *